(12) United States Patent
Sumathipala et al.

(10) Patent No.: US 10,859,560 B2
(45) Date of Patent: Dec. 8, 2020

(54) BIOSENSORS FOR DETECTING CHOLESTEROL AND OXLDL IN BLOOD SAMPLE

(71) Applicants: Adriel Sumathipala, Ashburn, VA (US); Marissa Sumathipala, Ashburn, VA (US); Yohan Sumathipala, Ashburn, VA (US)

(72) Inventors: Adriel Sumathipala, Ashburn, VA (US); Marissa Sumathipala, Ashburn, VA (US); Yohan Sumathipala, Ashburn, VA (US)

(73) Assignee: Adriel Sumathipala, Ashburn, VA (US)

( * ) Notice: Subject to any disclaimer, the term of this patent is extended or adjusted under 35 U.S.C. 154(b) by 426 days.

(21) Appl. No.: 15/871,029

(22) Filed: Jan. 14, 2018

(65) Prior Publication Data
US 2018/0136190 A1 May 17, 2018

Related U.S. Application Data

(63) Continuation-in-part of application No. 14/922,172, filed on Oct. 25, 2015, now Pat. No. 9,885,663.

(51) Int. Cl.
*G01N 33/52* (2006.01)
*G01N 33/92* (2006.01)
(Continued)

(52) U.S. Cl.
CPC ..... *G01N 33/48707* (2013.01); *A61B 5/1455* (2013.01); *A61B 5/1486* (2013.01); *A61B 5/14546* (2013.01); *A61B 5/6898* (2013.01); *C12Q 1/001* (2013.01); *G01N 27/327* (2013.01); *G01N 33/5038* (2013.01); *G01N 33/523* (2013.01); *G01N 33/558* (2013.01); *G01N 33/92* (2013.01)

(58) Field of Classification Search
None
See application file for complete search history.

(56) References Cited

U.S. PATENT DOCUMENTS 8,304,204 B2 * 11/2012 Yamaguchi ............... C12Q 1/32
435/11
2007/0134811 A1 * 6/2007 Takeuchi ............. G01N 33/558
436/514

(Continued)

OTHER PUBLICATIONS

Wilson et al. "A low cost inkjet printed glucose test strip system for resource-poor settings" Journal of Diabetes Science and Technology. 2015. Vo.. 9(6) pp. 1275-1281 (Year: 2015).*

(Continued)

*Primary Examiner* — Cachet I Proctor

(57) ABSTRACT

The present invention provides biosensors for detecting cholesterol and OxLDL in blood sample. The present invention relates to a paper-based colorimetric biosensor and an electrochemical biosensor each for detecting cholesterol and OxLDL in blood sample. The biosensors are inexpensive, rapid, simple, portable, diagnostics that incorporate information from multiple biomarkers associated with cardiovascular disease. The biosensors provide diagnostic test results that would place vital health data in the hands of doctors and patients and thus establish a framework for further advances in personalized medicine.

7 Claims, 17 Drawing Sheets

Working of the colorimetric cholesterol biosensor (100) for detecting cholesterol.

(51) Int. Cl.
  *G01N 33/487*   (2006.01)
  *G01N 33/50*    (2006.01)
  *C12Q 1/00*     (2006.01)
  *G01N 27/327*   (2006.01)
  *A61B 5/145*    (2006.01)
  *A61B 5/1486*   (2006.01)
  *A61B 5/00*     (2006.01)
  *A61B 5/1455*   (2006.01)
  *G01N 33/558*   (2006.01)

(56) References Cited

U.S. PATENT DOCUMENTS

| | | | | |
|---|---|---|---|---|
| 2010/0099125 | A1* | 4/2010 | Yamaguchi | C12Q 1/44 435/11 |
| 2011/0111517 | A1* | 5/2011 | Siegel | B01L 3/502707 436/164 |
| 2011/0286896 | A1* | 11/2011 | Hess | D21H 21/16 422/503 |
| 2011/0306072 | A1* | 12/2011 | Nicholls | G01N 33/92 435/11 |
| 2012/0122197 | A1* | 5/2012 | Jospeh | G01N 27/3272 435/283.1 |
| 2016/0207039 | A1* | 7/2016 | Vella | D21H 21/16 |

OTHER PUBLICATIONS

Oncescu et al. "Cholesterol testing on a smartphone". Lab Chip, 2014, 14 pp. 759-763 (Year: 2014).*

* cited by examiner

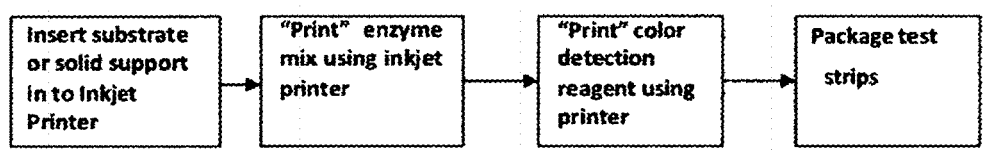
Figure 1A: Schematic diagram of the preparation of the detector strip using an inkjet printer.

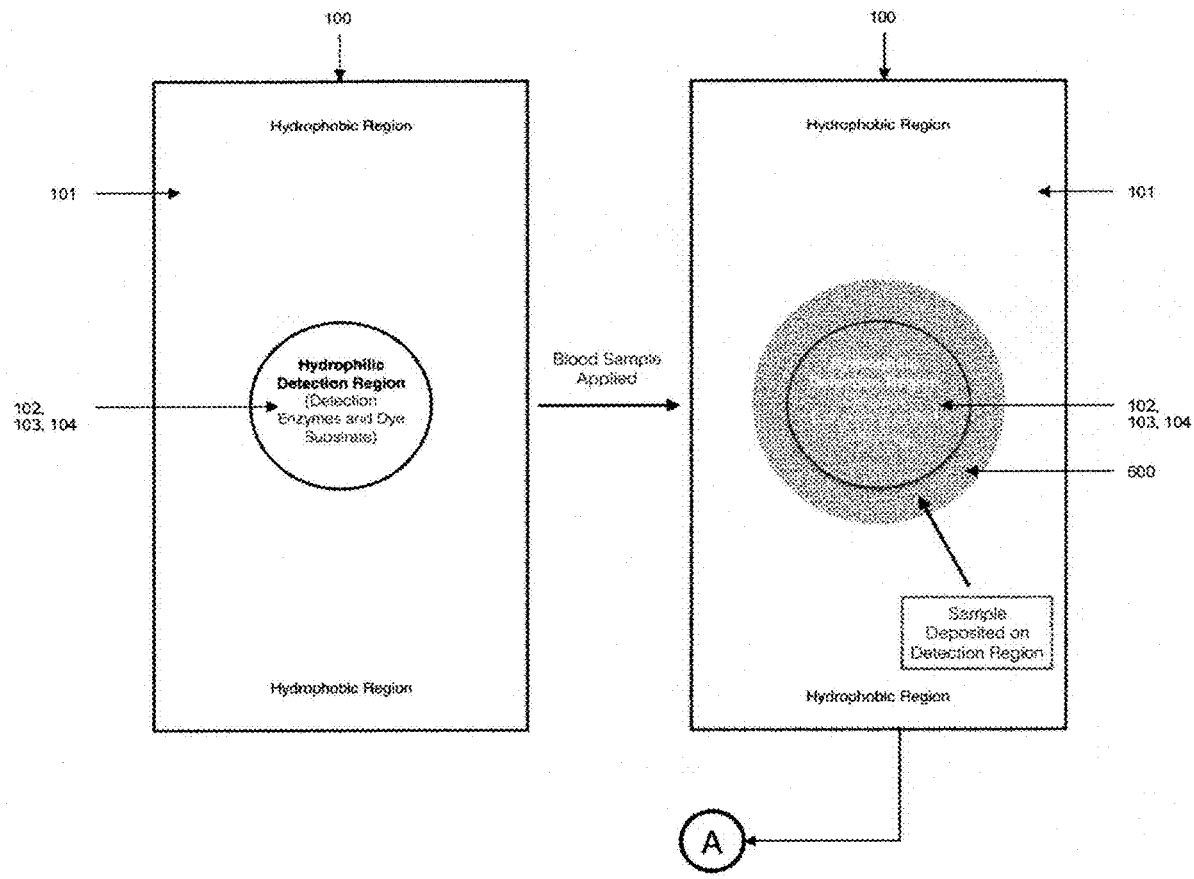
Figure 1B: Working of the colorimetric cholesterol biosensor (100) for detecting cholesterol.

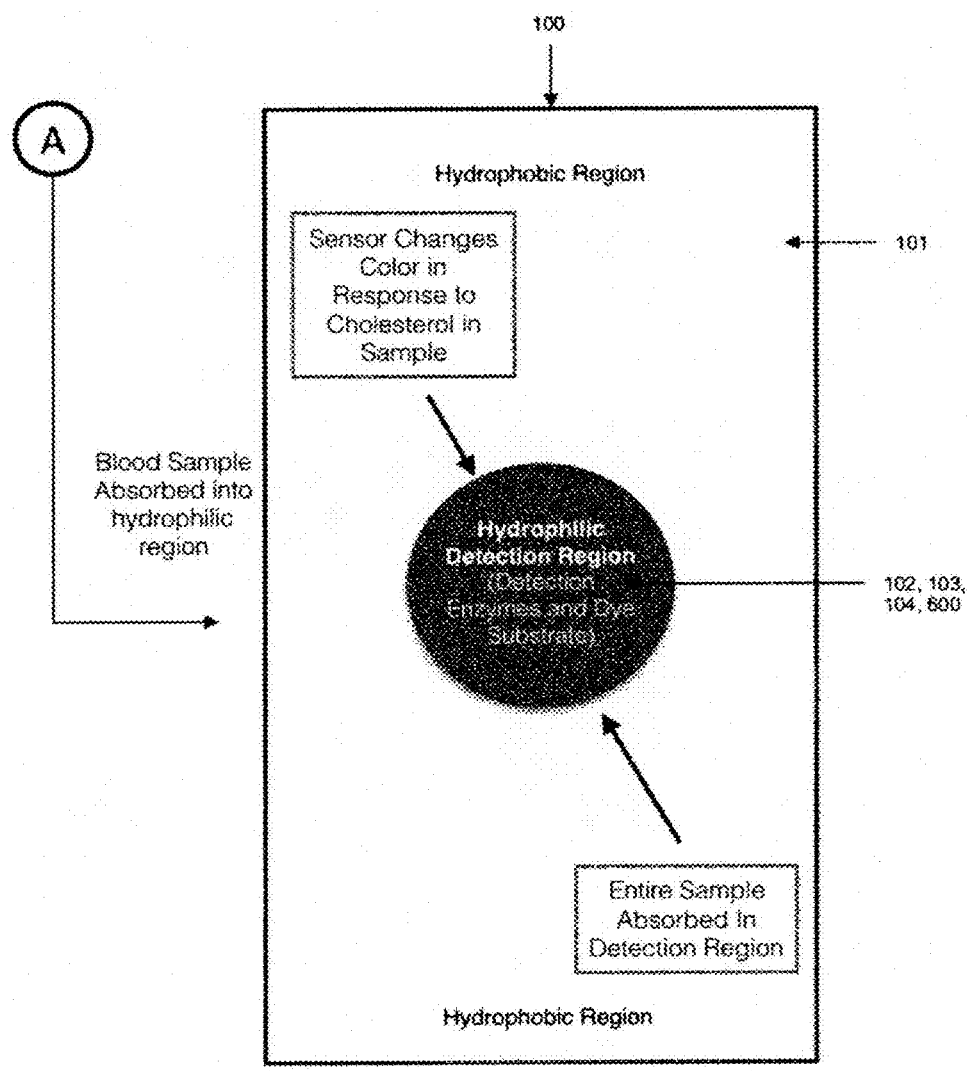
Figure 1C: Working of the colorimetric cholesterol biosensor (100) for detecting cholesterol.

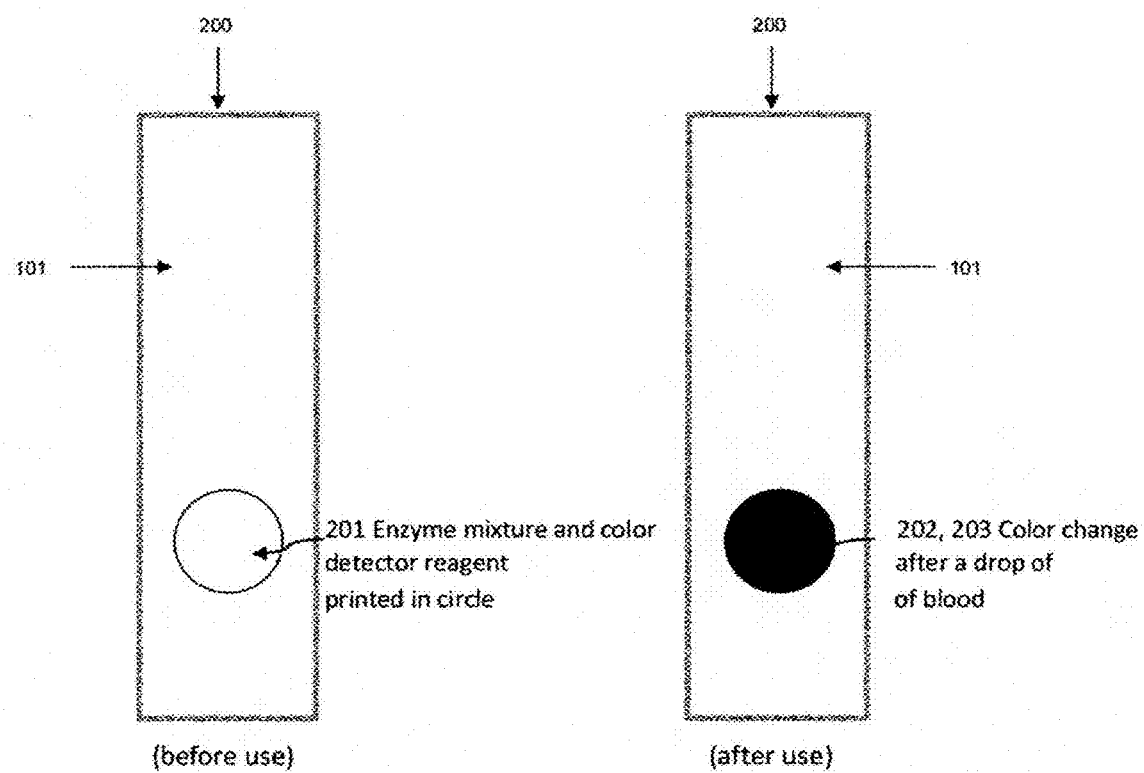
Figure 2: Schematic diagram of colorimetric biosensor, before and after use.

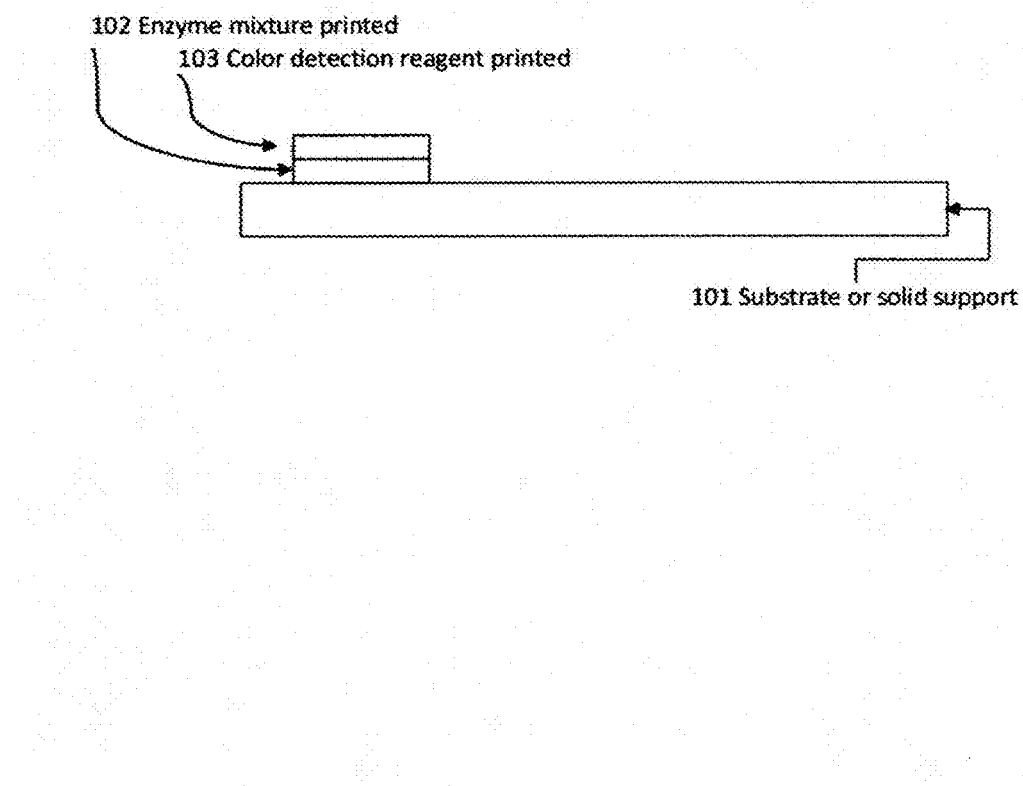
Figure 3: Side view schematic depiction of test strip layers, including printed reagent mixture and color detection reagent

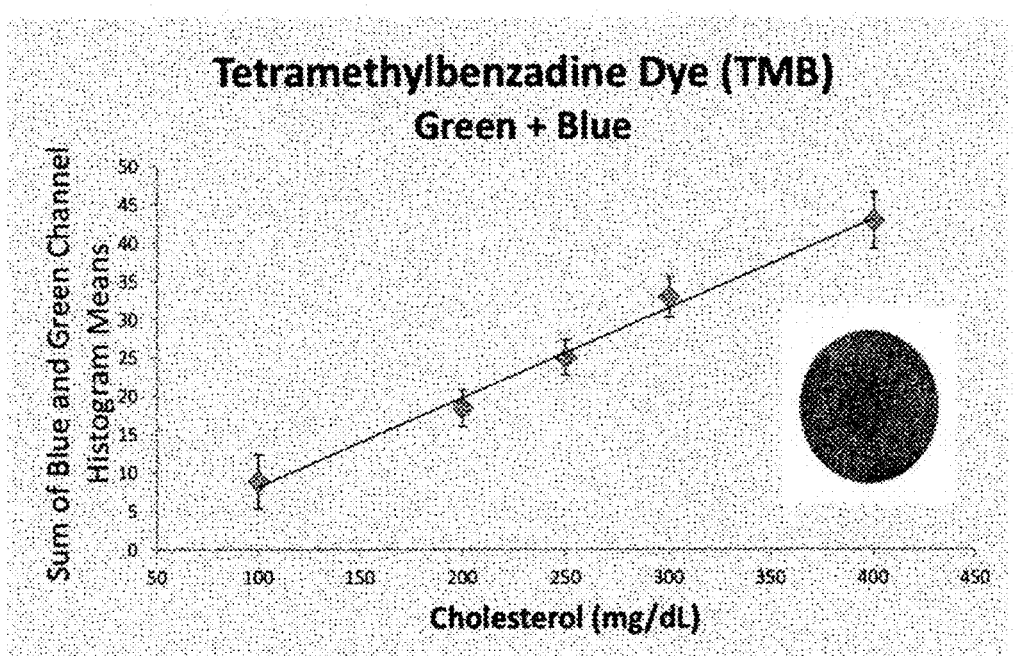
Figure 4: Variation of color intensity with concentration of cholesterol in the presence of Tetramethylbenzadine as the color detection reagent

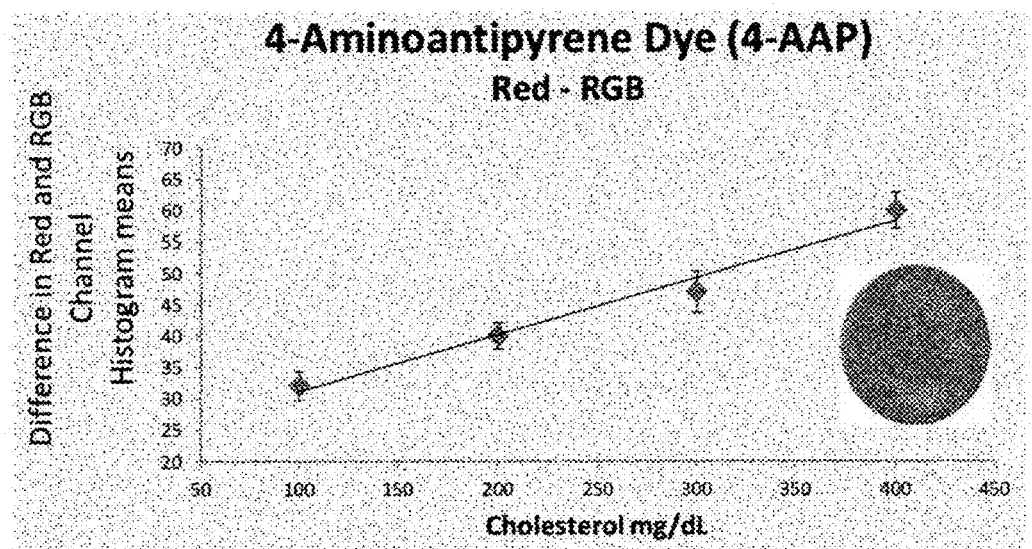
Figure 5: Variation of color intensity with concentration of cholesterol in the presence of 4-Aminoantipyrene as the color detection reagent

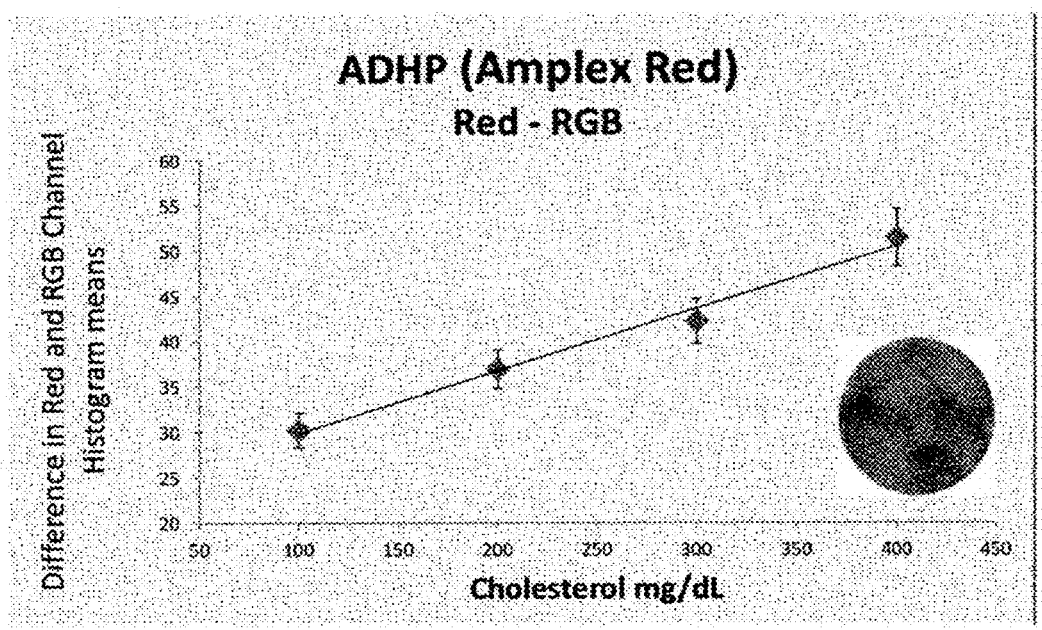
Figure 6: Variation of color intensity with concentration of cholesterol in the presence of Amplex Red as the color detection reagent

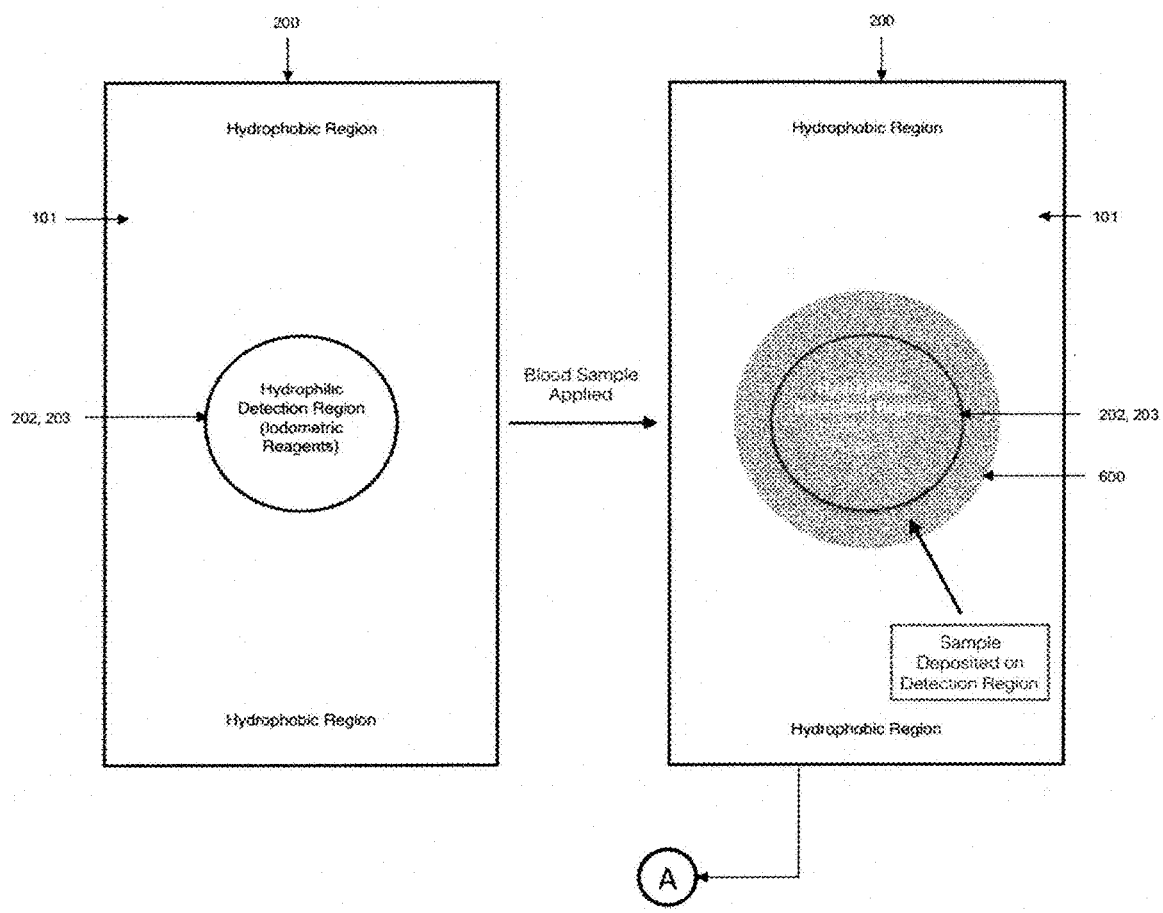
Figure 7A: Working of the colorimetric OxLDL biosensor (200) for detecting OxLDL.

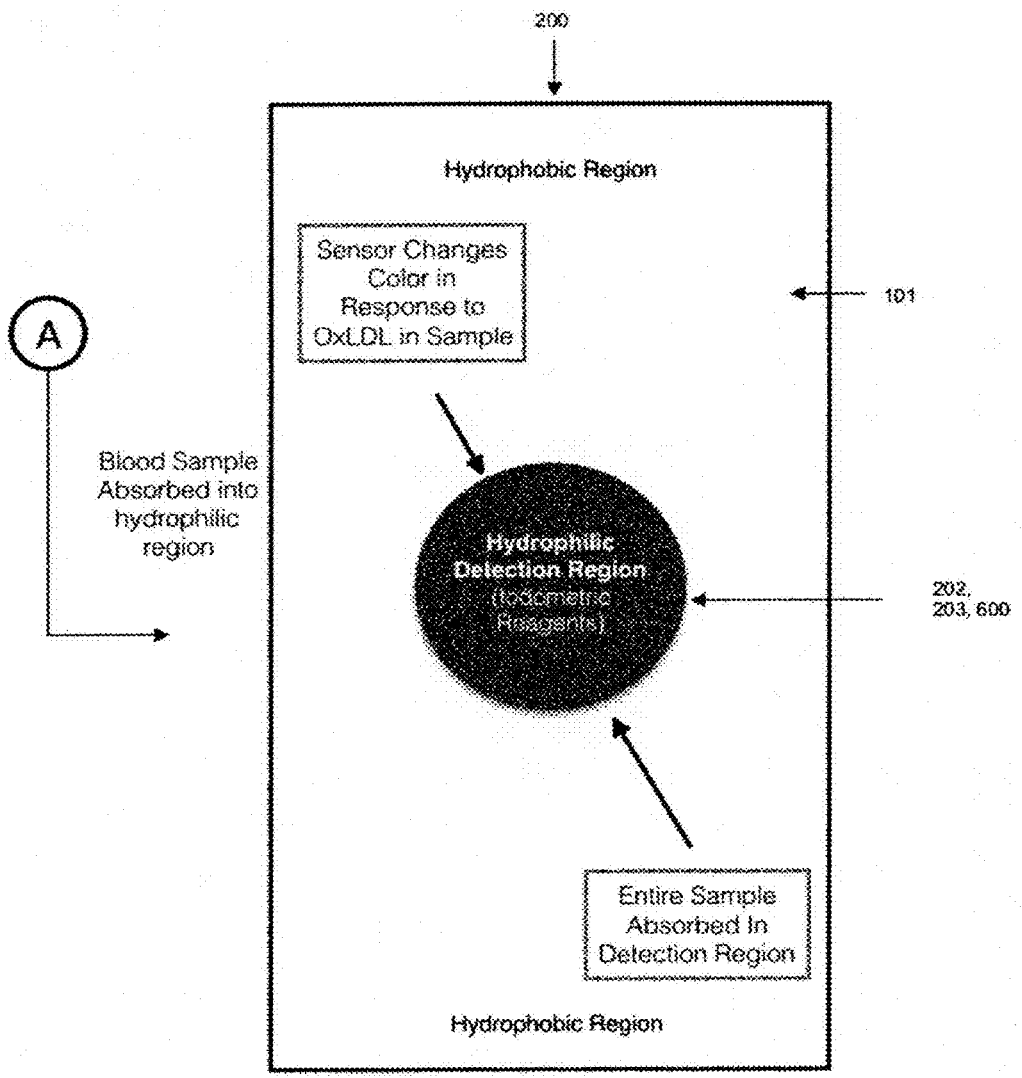
Figure 7B: Working of the colorimetric OxLDL biosensor (200) for detecting OxLDL.

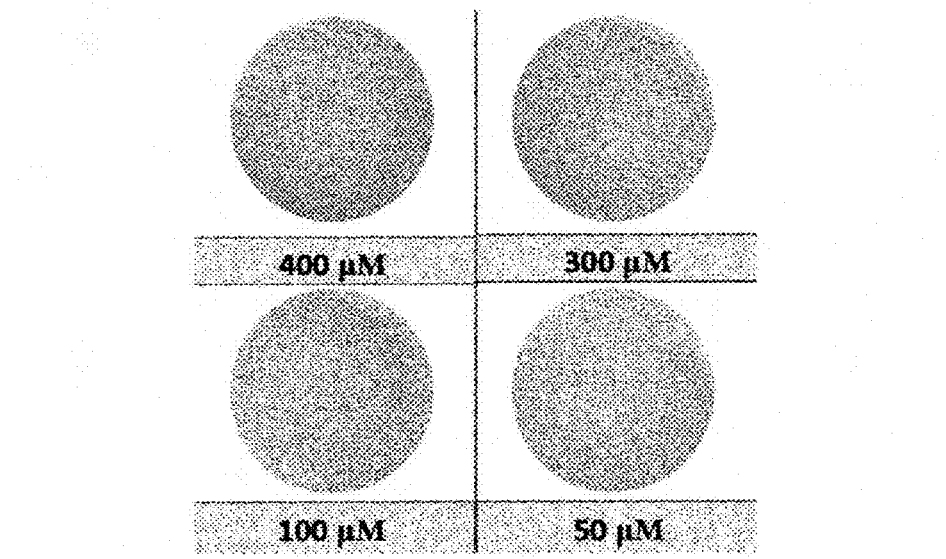
Figure 7C: Colorimetric OxLDL biosensor's response to varying concentrations of hydrogen peroxides.
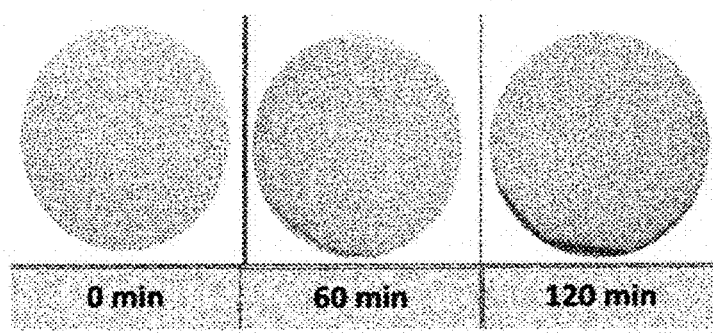
Figure 7D: Colorimetric OxLDL biosensor's response to OxLDL at 0, 60, and 120 minute time intervals of the oxidative process.

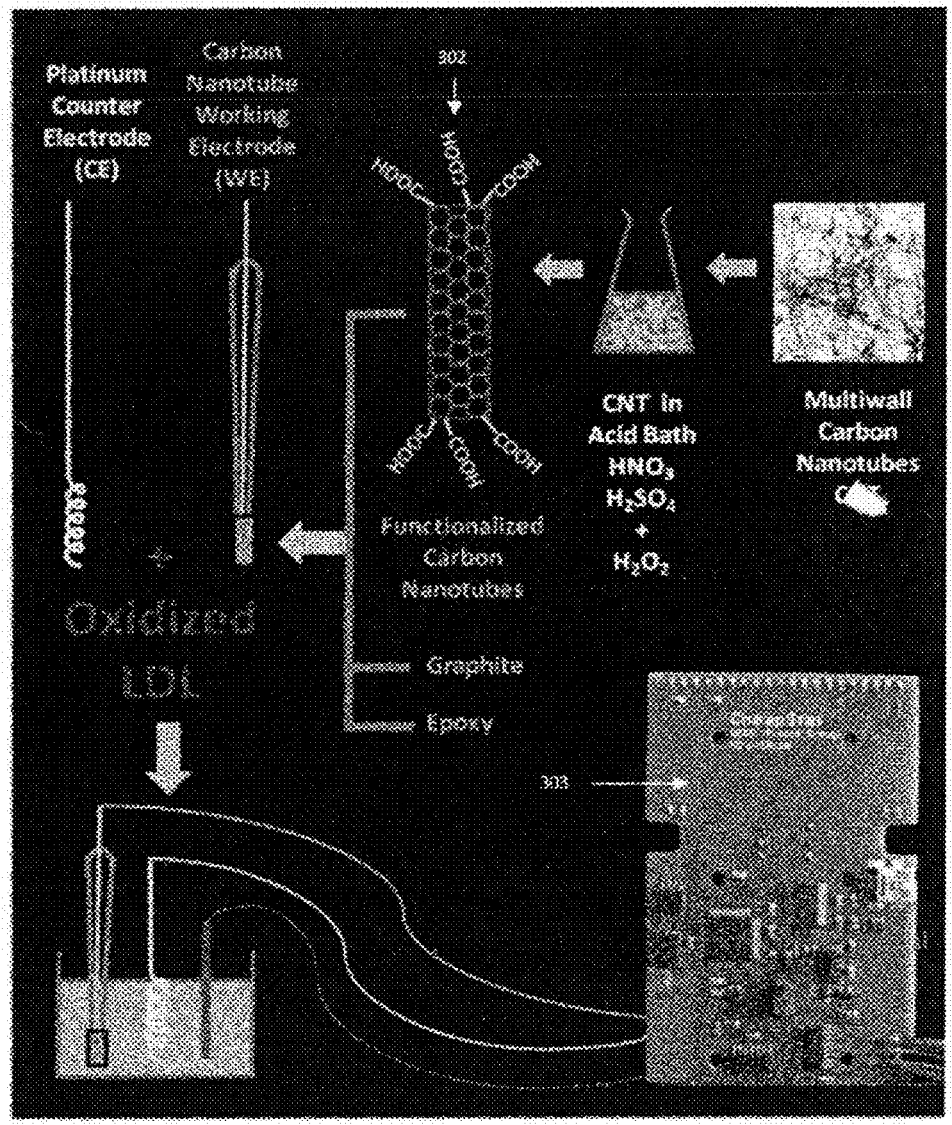
Figure 8: Schematic diagram of electrochemical biosensor for detecting OxLDL.

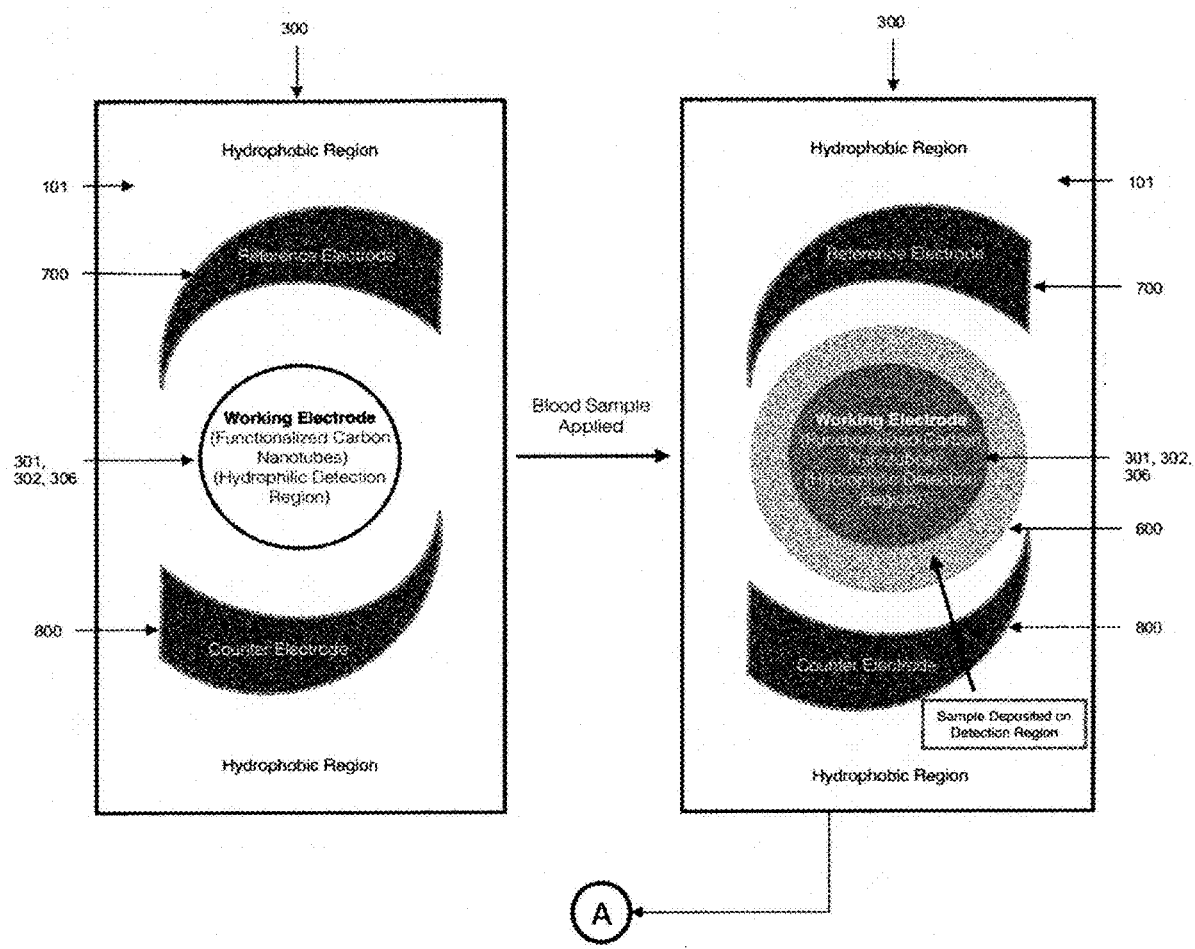
Figure 9A: Working of electrochemical OxLDL biosensor for detecting OxLDL.

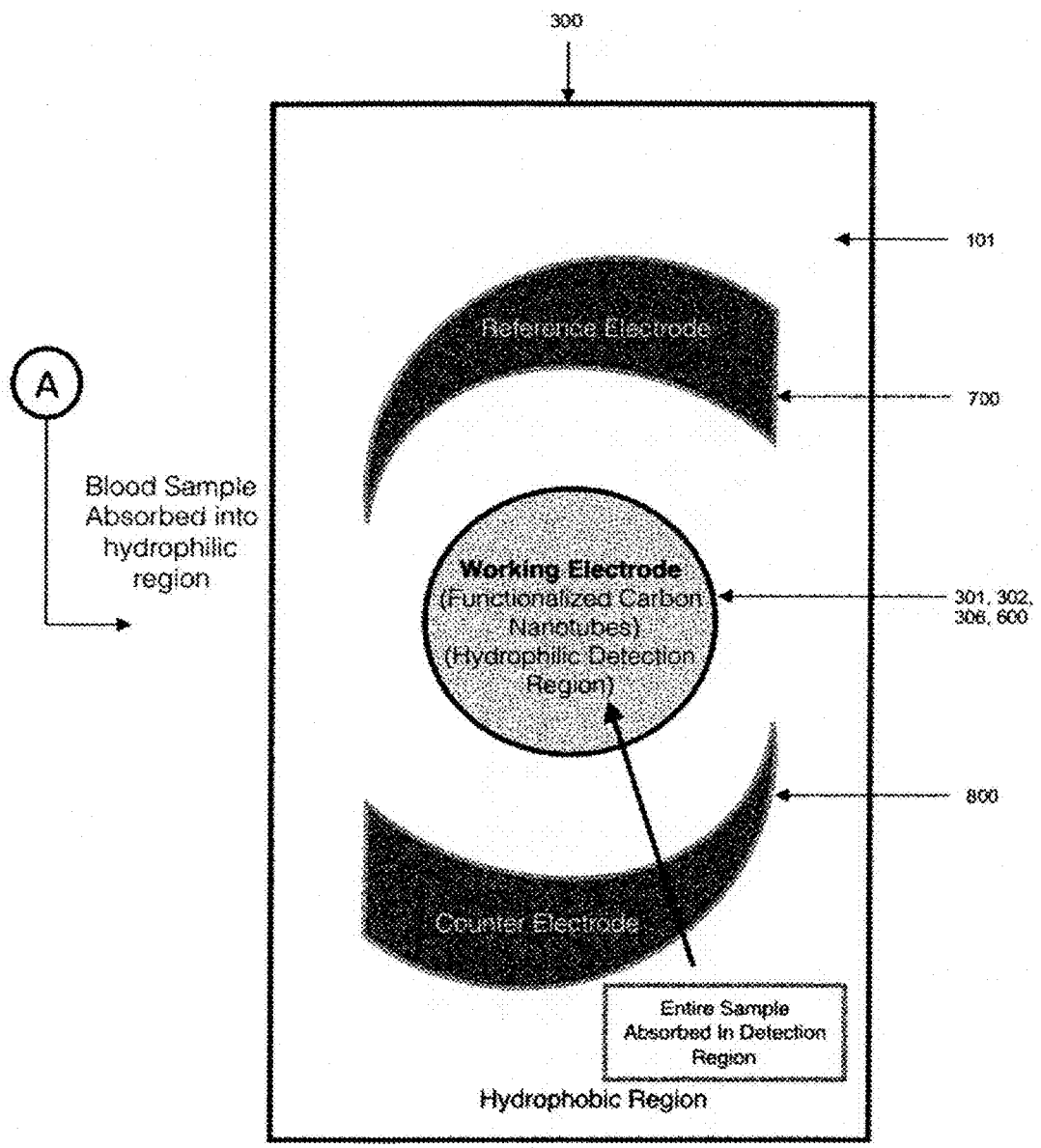
Figure 9B: Working of electrochemical OxLDL biosensor for detecting OxLDL.

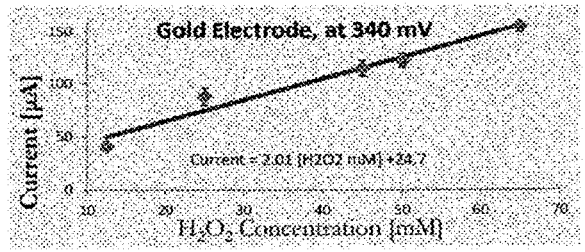
Figure 10A: Sensitivity of the gold working electrode to hydrogen peroxides.
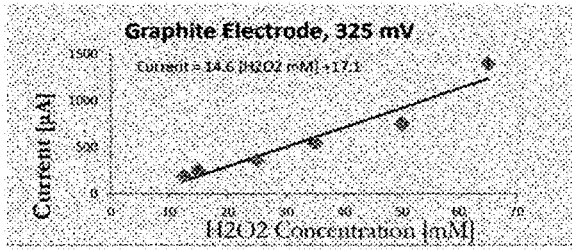
Figure 10B: Sensitivity of the graphite working electrode to hydrogen peroxides.
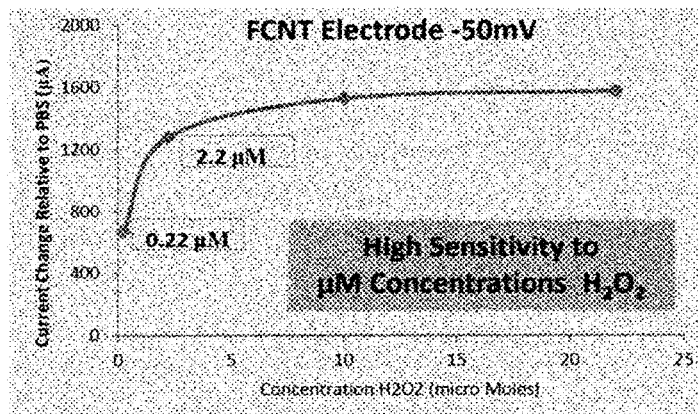
Figure 10C: Sensitivity of the functionalized carbon nanotube working electrode to hydrogen peroxides.
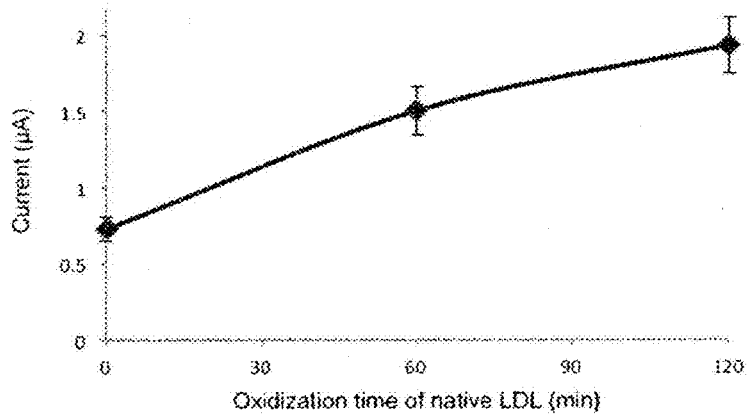
Figure 10D: OxLDL electrochemical sensor's response to the oxidation of native LDL over time.

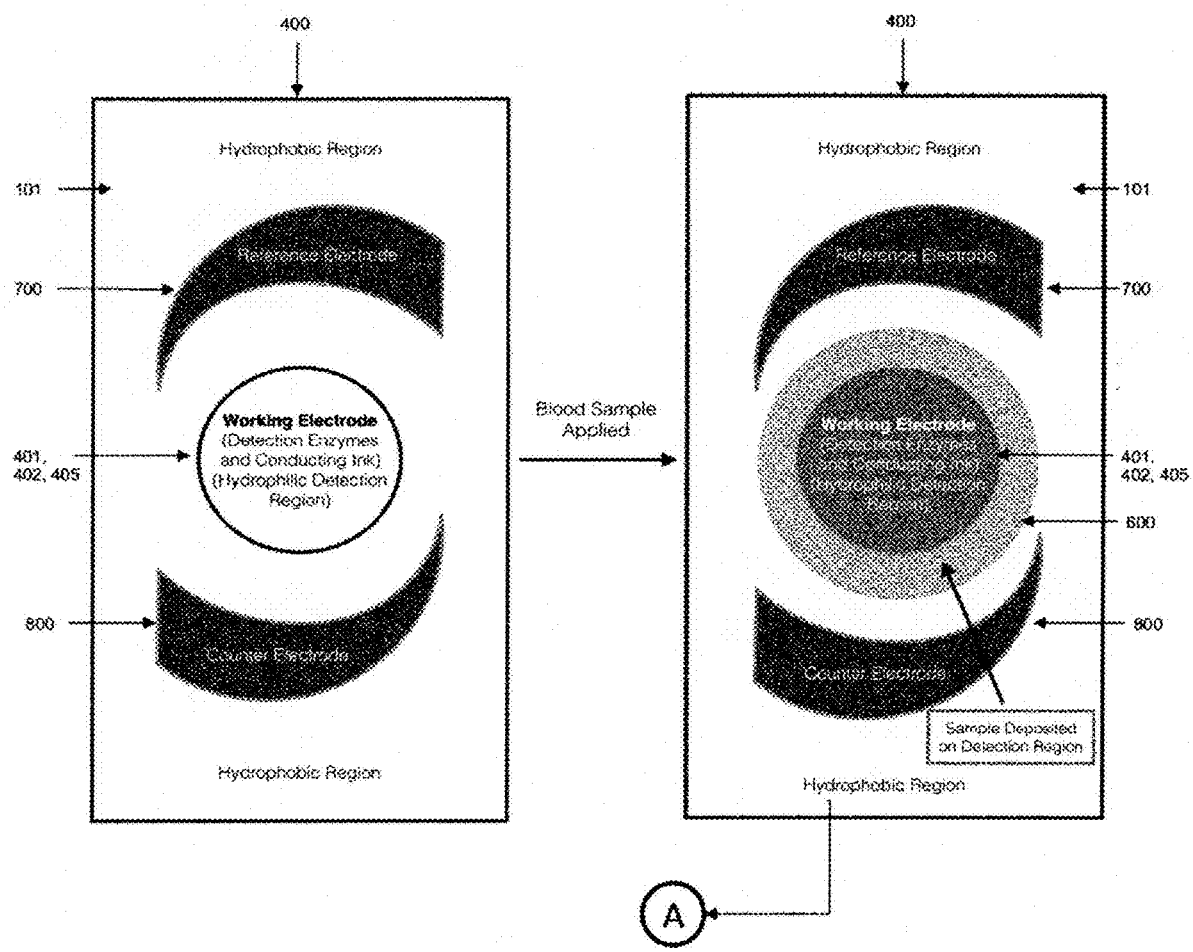
Figure 11A: Working of electrochemical cholesterol biosensor for detecting cholesterol.

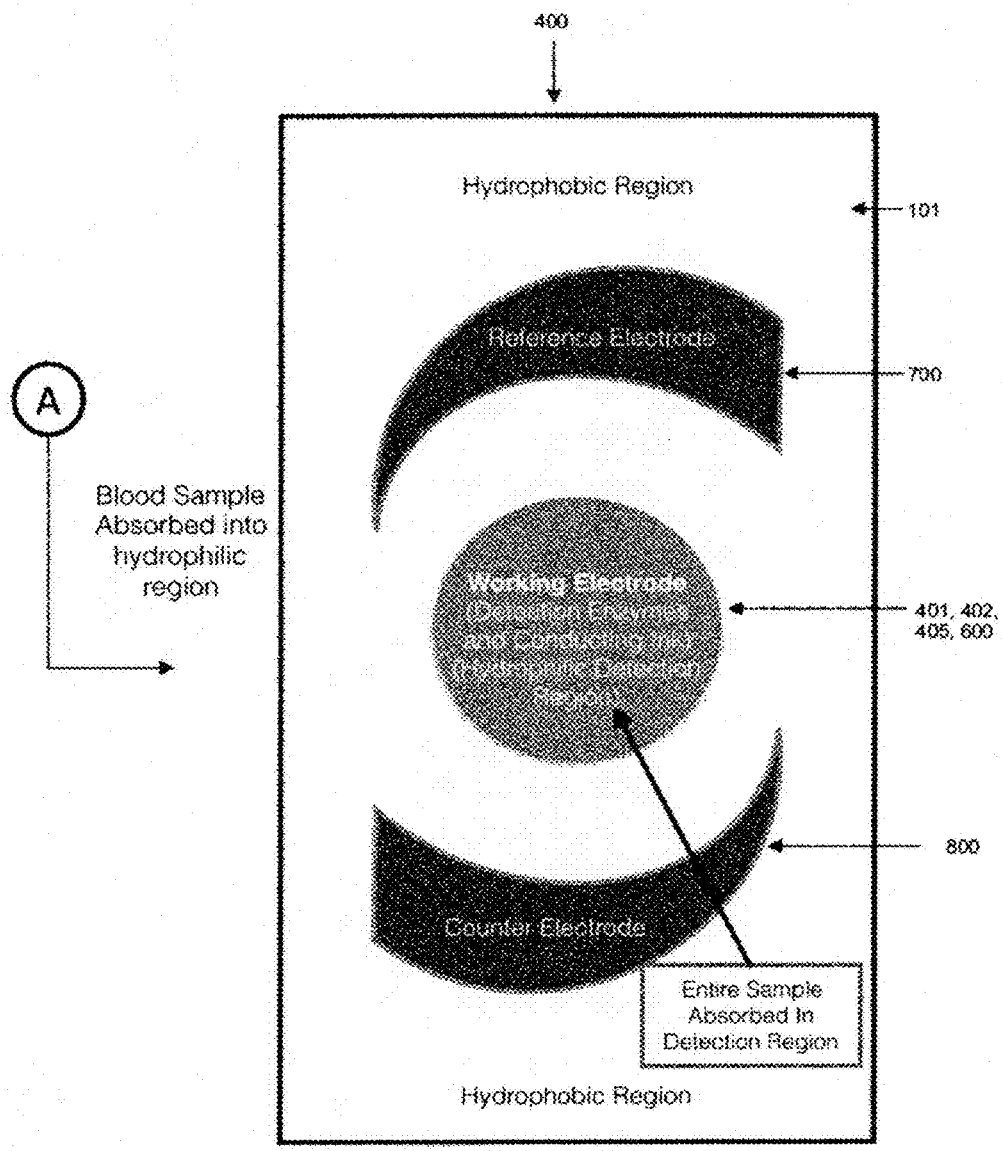
Figure 11B: Working of electrochemical cholesterol biosensor for detecting cholesterol.

BIOSENSORS FOR DETECTING CHOLESTEROL AND OXLDL IN BLOOD SAMPLE

CROSS-REFERENCE TO RELATED APPLICATION

This application is a continuation-in-part (CIP) of U.S. patent application Ser. No. 14/922,172 entitled "Portable, Rapid, and Inexpensive Diagnostic Test for Cardiac Disease Risk". This patent was allowed on Nov. 3, 2017 and is awaiting issuance.

FIELD OF INVENTION

The present invention relates to biosensors for detecting cholesterol and OxLDL in a blood sample. In particular, the present invention relates to a paper-based colorimetric biosensor and an electrochemical biosensor for detecting cholesterol and OxLDL in a blood sample.

BACKGROUND OF INVENTION

Cardiovascular disease is the preeminent cause of morality in the world, more so than cancers, respiratory ailments, or infectious diseases. Cardiovascular disease is expensive to treat and would be much cheaper to prevent if patients had a way to identify their risk level. This invention makes it possible for early diagnosis as well as quantification of the risk level.

Similar to other diseases that require long term treatment, such as HIV and cancer, detection of cardiovascular disease is essential for successful treatment. Additionally, the treatment is individual-specific and require continuous monitoring of the risk level. The invention described here allow for a fast, portable, and inexpensive diagnostic method.

Present diagnostics for cardiac disease are lab-based, require large sample volumes, expensive, take long time to report results, and are, as a result, infrequently conducted. As a result, many high-risk patients are often unaware of their risk level and the possible need for lifestyle changes to lower their risk level.

According to the World Health Organization (WHO), cardiovascular disease is responsible for an estimated 17.5 million deaths in 2012 or 31% of all global deaths. In the United States alone, cardiovascular disease is responsible for every third death, claiming more lives than all cancers combined. Moreover, cardiovascular disease is a problem in both developing and developed states with 80% of cardiovascular deaths occurring in low to middle income countries (LIMCs), at younger ages than in high-income countries.

Cardiovascular disease, compounding its global presence in both developing and developed states, costs the United States alone 444 billion USD annually to treat, with each incidence of cardiovascular arrest costing an average of $760,000. This equates to one out of every six dollars spent on health care in the United States, making cardiovascular disease one of the most expensive diseases to treat. According to the World Health Organization's estimates, given current spending in LIMCs and accounting for inflation, cardiovascular disease treatment will cost 3.76 trillion dollars to treat from 2011-2025. As a result, the World Health Organization and American Heart Association advocate that early diagnosis and lifestyle changes are the most economically prudent policies to combat cardiovascular disease.

Like HIV and cancer, early detection of cardiovascular disease is crucial to ensure long-term treatment can begin, improving patient's quality of life and reducing the risk of premature death. There is no single, simple treatment for the cardiovascular disease. Cardiovascular disease is best treated through long-term lifestyle management. Patients who seek to manage and monitor their risk for cardiovascular disease need a rapid, accurate, and portable multi-biomarker diagnostic to assess cardiovascular risk and provide feedback on patient's lifestyle management. These diagnostics must be portable enough to be used in home, office, point-of-care and other diverse settings. Moreover, developing states, which lack advanced health infrastructure, require inexpensive diagnostics to diagnose cardiovascular disease.

The present diagnostics for diagnosing cardiac disease are lab-based and requires large volumes of blood samples. Further, they are expensive and require a significant amount of time to generate results. As a result, standard lipid and cholesterol tests run once every 6 months, on an average, due to the high cost involved with testing. Because of the resource-intensive nature of current cardiac disease diagnostics, cardiovascular disease often goes undiagnosed in LIMCs with under-developed healthcare infrastructures. Additionally, in developed states, tests for cardiovascular disease risk are run infrequently, generally once every six months. The current lab-based tests, in addition to aforementioned deficiencies, use complex procedures such as the multi-step sandwich enzyme-linked immunosorbent assays (sandwich ELISAs) which necessitate specialized lab equipment and trained lab technicians.

Cardiac disease's pathogenesis is largely attributed to cholesterol, predominantly carried by low-density lipoproteins (LDL). Conventionally, the standard diagnostic tests target a single biomarker—blood cholesterol. However, current tests only measure total blood cholesterol (TBC) and cholesterol within high-density lipoproteins (HDL-C) and low-density lipoproteins (LDL-C). Furthermore, LDL-C is not measured directly in these tests, but rather estimated using TBC and LDL-C. Cholesterol biomarkers, especially LDL-C and TBC, do not accurately discriminate healthy and diseased individuals; individuals with both high and low concentrations of current biomarkers may have similar risk of cardiac disease due to their weak correlation with cardiac disease.

However, recent research has discovered a new biomarker of cardiac disease namely an oxidized-LDL (hereafter OxLDL), which has a far stronger correlation with cardiac disease than any current biomarkers. This is because OxLDL generates an immune response and is swarmed by masses of immune cells. These immune cells ingest OxLDL and become foam cells which form plaque, the hallmark of cardiac disease. OxLDL is devastatingly potent in its ability to initiate and accelerate atherosclerosis, the formation of plaque in artery walls. The tests for both cholesterol and OxLDL are lab-based and expensive. The standard OxLDL tests, performed at selected labs, are highly specialized and are costlier than cholesterol tests. Furthermore, these tests only detect the oxidization of LDL in its final stage of the oxidative process, when irreversible conformational changes occur to the apolipoprotein-$\beta$ of LDL. Evidently, a need exists to detect OxLDL at early stages of oxidation to enable early detection of cardiac disease.

US Patent application US 2012062436A2, by Abner D. Joseph, discloses an inkjet deposition for general biosensor manufacturing. However, there is a need for a rapid and inexpensive diagnostic test specifically for cardiac disease.

The iodometric reaction shown by El-Saadani et al. detects lipid peroxides (ROOH) on the OxLDL molecule.

The reaction produces a yellow triiodide ion. This work's reliance on incubation, spectrophotometric absorption analysis, and large sample volume make it a lab-only test.

Further, as noted in the above prior art, the traditional approaches for applying reagent to diagnostic test strips for cardiac disease diagnostics, such as traditional slot-die coating, drop deposition techniques, and screen or rotary printing techniques, have significant drawbacks, such as manufacturing line speed limitations, quality issues, and reagent waste. Hence, there is a need to overcome several inherent limitations in the traditional production of test strips for the detection of cardiovascular disease.

In view of the aforementioned time, portability, and cost deficiencies associated with prior art diagnostics, testing and methods, it should be apparent that there exists a great need in the art for inexpensive, rapid, simple, portable diagnostics that incorporate information from multiple biomarkers associated with cardiovascular disease. Furthermore, an economically prudent system to manufacture a diagnostic and a mobile platform to analyze and quantify the diagnostic's results are needed. The diagnostic and quantification system must be portable and simple enough for non-specialists, including but not limited to patients, and care providers, to use in a variety of settings, including, but not limited to, homes, offices, and point-of-care settings.

BRIEF DESCRIPTION OF THE DRAWINGS

FIG. 1A: Shows the schematic diagram of the preparation of the detector strip using inkjet printer.

FIG. 1B and FIG. 1C: Shows working of the colorimetric cholesterol biosensor (100) for detecting cholesterol.

FIG. 2: Shows the schematic diagram of the colorimetric biosensor, before and after diagnosis.

FIG. 3: Shows the side view of a schematic depiction of test strip layers, including printed reagent.

FIG. 4: Shows the variation of color intensity with concentration of cholesterol in the presence of Tetramethylbenzadine as the color detection reagent. Where, the data shows, the average of green and blue color intensity values and the error bars indicate, the variation of color intensity measured in multiple test strips. These color intensities correlate with the concentration of cholesterol present in the sample.

FIG. 5: Shows the variation of color intensity with concentration of cholesterol in the presence of 4-Aminoantipyrene as the color detection reagent. Where, the data shows the difference between the red and average of RGB intensity values and the error bars indicate the small variation of color intensity measured in multiple test strips. These color intensities correlate with the concentration of cholesterol present in the sample.

FIG. 6: Shows the variation of color intensity with concentration of cholesterol in the presence of 10-Acetyl-3,7-dihydroxyphenoxazine, commonly referred to as Amplex Red, as the color detection reagent. Where, the data shows the difference between the red and average of RGB intensity values and the error bars indicate the small variation of color intensity measured in multiple test strips. These color intensities correlate with the concentration of cholesterol present in the sample.

FIG. 7A and FIG. 7B: Shows the working of the colorimetric OxLDL biosensor (200) for detecting OxLDL.

FIG. 7C: Shows the colorimetric OxLDL biosensor's response to varying concentrations of hydrogen peroxides. Hydrogen peroxides were used as a proxy molecule for OxLDL in the development of the disclosed diagnostics.

FIG. 7D: Shows the colorimetric OxLDL biosensor's response to OxLDL at 0, 60, and 120 minute time intervals of the oxidative process.

FIG. 8: Shows the schematic diagram of electrochemical biosensor for detecting OxLDL.

FIG. 9A and FIG. 9B: Shows the working of electrochemical OxLDL biosensor for detecting OxLDL.

FIG. 10A: Shows the sensitivity of the gold working electrode to hydrogen peroxides.

FIG. 10B: Shows the sensitivity of the graphite working electrode to hydrogen peroxides.

FIG. 10C: Shows the sensitivity of the functionalized carbon nanotube working electrode to hydrogen peroxides.

FIG. 10D: Shows the OxLDL electrochemical sensor's response to the oxidation of native LDL over time.

FIG. 11A and FIG. 11B: Shows the working of electrochemical cholesterol biosensor for detecting cholesterol.

DETAIL DESCRIPTION

Cholesterol Colorimetric Test

One of the embodiments of the present invention is to provide a cholesterol colorimetric biosensor (100) for accurately detecting cholesterol in a blood sample. The cholesterol biosensor (100) is a portable, significantly low-cost, paper-based sensing platform which detects the blood cholesterol using a colorimetric detection method. The cholesterol biosensor (100) is fabricated by depositing reagents on a detection test strip (101) using an inkjet printer. The reagents are either enzyme mixture reagent (102) or color detection reagent (103) or a combination of both. The test strip (101) is a substrate or solid support, capable of absorbing the reagents. The substrate includes Whatman Grade 1 qualitative filter paper.

FIG. 1A shows the schematic diagram of the test strip (101) development. As shown, the test strip (101) is placed in the inkjet printer paper tray and the enzyme mixture reagent (102) (enzyme ink) is placed in an ink cartridge of the inkjet printer. The enzyme mixture reagent (102) is printed on the test strip (101) in a predetermined shape. The color detection reagent (103) is then placed in the ink cartridge of the inkjet printer and is printed over the enzyme mixture reagent (102) on the test strip (101). The mixture of enzyme mixture reagent (102) and color detection reagent (103) is herein referred to as "reagent ink".

The enzyme mixture reagent (102) comprises of: enzymes including horseradish peroxidase, cholesterol oxidase and glucose oxidase to detect cholesterol; ionic salt buffer solution; Phosphate-buffered saline 1× (PBS), surfactant including triton X-100 and sodium n-dodecyl sulfate; humectant including glycerol and polyethylene glycol.

The color detection reagent (103) comprises of: surfactant including triton X-100 and sodium n-dodecyl sulfate; humectant including glycerol and polyethylene glycol and chromogenic dye selected from Tetramethylbenzidine (TMB), 4-Aminoantipyrine (4-AAP) or Acetyl-3,7-dihydroxyphenoxazine (ADHP). The ionic salt buffer solution includes phosphate buffer saline to preserve protein structures.

FIG. 1B and FIG. 1C shows the working of the biosensor (100). The hydrophilic sample receiving region (104) is provided on top of the area where the enzyme mixture reagent (102) and color detector reagent (103) are printed. The region of the sensor surrounding the sample receiving region is hydrophobic. Thus, when the sample is placed on the sensor, the entire sample is absorbed only in the receiving region where the enzyme mixture reagent and color detector reagent are printed. When a sample of blood (600) is placed over the sample receiving region (104), the biosensor (100) changes the color in the detection strip (101). The change of the color is due to the redox reaction shown below that occurs in the presence of enzymes and chromogenic dye.

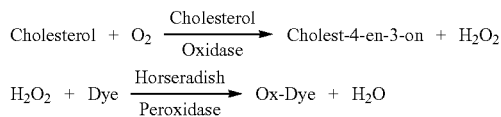

Once the color fully develops, an image of the blood sample is captured using a smartphone camera for RGB histogram analysis. It will be appreciated by those skilled in the art that any other suitable imaging platform may be used to capture the image. The color change indicates the amount of cholesterol in the blood sample. Thus, cholesterol levels are successfully quantified by the inkjet-printed biosensors (100) utilizing the smartphone camera for image capture.

FIG. 2 illustrates the detector strip (101) before and after diagnosis. As indicated by (105), the enzyme mixture reagent (102) and the color detector reagent (103) are printed as circles on the substrate or solid support (101). While a circular shape of printed enzyme mixture reagent (102) and color detector reagent (103) is shown for illustration purposes, other shapes and sizes may also be printed. When a sample of blood (600) is placed over the enzyme mixture reagent (102) and color detector reagent (103) is present in the detection strip (101), the color changes depending upon the cholesterol level detected in the blood sample as indicated by (106).

FIG. 3 shows the present invention, where a layer of enzyme mixture reagent (102) is first applied by the inkjet printer on the test strip (101). The color detection reagent (103) is then applied by the inkjet printer on top of the enzyme mixture reagent (102). It should not, however, be considered as a limitation of scope of the present invention that the enzyme mixture reagent (102) and color detection reagent (103) are applied as two separate layers on the test strip (101). The enzyme mixture reagent (102) and color detection reagent (103) may be applied as one mixture or multiple layers. When the enzyme mixture reagent (102) and color detection reagent (103) are printed as a single mixture, the mixture comprises of: enzymes including horseradish peroxidase, cholesterol oxidase and glucose oxidase; PBS 1×; ionic salt buffer solution; surfactant including triton X-100 and sodium n-dodecyl sulfate; humectant including glycerol and polyethylene glycol and dye is selected from Tetramethylbenzidine (TMB), 4-Aminoantipyrine (4-AAP) or Acetyl-3,7-dihydroxyphenoxazine (ADHP).

The substrate or solid surface (101) onto which reagents are applied by inkjet printing may be a flat surface or may have depressions, such as indentations, grooves and wells. The depressions are created by multilayer substrate where cutouts have been formed on some of the layers. The depositing of reagents into such depressions on the substrate or solid surface is accomplished by conveniently reprogramming the computer driving the inkjet printer. Inkjet printers produce droplets in the range of 2 to 4 Pico liters, giving the ability to apply reagents uniformly and also to control the reagent film thickness precisely. This enables the development of accurate and repeatable detection test strips.

Inkjet printing, however, requires a robust formulation of the reagent to minimize the impact on the reagent activity of enzymes. The present invention overcomes several significant obstacles in order to produce formulations that overcomes this limitation. Further, inkjet printing is optimized for viscosity and surface-tension to prevent clogging and dripping during printing.

When developing the reagent ink, a number of significant factors and issues are eliminated. Several factors of ink rheology affect the thickness and uniformity of the printed reagent film. Inkjet printing rheology are subjected to narrower limitations when compared with the traditional methods of slot-die coating or screen printing. Specifically, inkjet printing requires ink that has high shear thinning properties and a narrow range of viscosity. For example, bubble thermal jet printers operate with ink formulations in the range of 1-3 cP viscosity, whereas piezoelectric inkjet printing ink works best in a viscosity range of 6-12 cP. In either method, the enzyme formulation should be able to withstand the shear produced by the inkjet head without losing activity.

The rheology of the selected reagents is such that the inkjet printer is capable of applying the reagents to the test strip (101) and the reagents bind directly or indirectly with the test strip (101) along with other reagents already present on the test strip (101). The reagents bind covalently or non-covalently to the test strip. The reagents are applied in varying patterns and of varying concentrations or dilutions on the substrate. The present invention enables printing of different reagent formulations on the test strip (101) for detecting multiple diseases. Additionally, the present invention allows multi-layer printing with reagents in different layers. Shape, thickness, and number of layers of reagents is configured by changing the printing pattern on a computer. This ability to swiftly reconfigure the test strip (101) avoids retooling and machine stoppages required in the traditional approaches for developing detection test strips.

The use of triton X-100 as a surfactant provides the needed reduction of surface tension in the reagent ink rheology so as to be printable with an inkjet printer. Other types of surfactants, such as ionic surfactants, are also suitable for this purpose; however, they may degrade enzyme activity. Additionally, triton X-100 provides fast wetting of the substrate and control of dispersal of reagent ink. Reagent ink formulations with high surface tension tend to not deposit reagent ink properly, especially when not mixed properly, and reagent ink formulations with low surface tension tend to spread beyond the area of printing. Neither condition produces a desirable test strip.

After placement of the blood on the test strip, a red blood cell filter is optionally added on top of the sample receiving region (104) to remove red blood cells, leaving only blood plasma. The red blood cell filter is a lectin-treated and has a narrow pore size. The red blood cell filter increases the accuracy of colorimetric method in detecting cholesterol by eliminating background colorations from red blood cells.

Hydrophobic reagent ink (500a) is optionally added to improve lateral flow characteristics by limiting the region of flow on the test strip (101). The hydrophobic reagent ink (500a) is printed around the sample receiving region (104) on the substrate or solid surface (101) using an inkjet printer. The hydrophobic reagent ink (500a) creates channels and regions on paper substrate. Once deposited onto the substrate (101), the hydrophobic reagent forms hydrophobic regions (500) to prevent water or aqueous solutions such as blood from being absorbed into the substrate. The aqueous solution rests on top of the hydrophobic region (500), exhibiting a high contact angle. This ensures absorption of the blood sample (600) only on the testing regions (104) where the detection reagents are present. This decreases the amount of blood sample required to perform the test, ensuring blood draws are faster and more comfortable for the patient. The hydrophobic reagent ink (500a) comprises of: hydrophobic sizing agent including alkenyl succinic anhydride (ASA) to make certain regions of test strip hydrophobic; organic solvent including acetone, benzene and hexanol to solubilize hydrophobic sizing agent; surfactant including triton X-100 and sodium n-dodecyl sulfate and humectant including glycerol and polyethylene glycol.

Experimental Data:

To ensure if chemistry of the biosensor (100) is reliable and accurate before printing the sensor, a mixture of enzymes, dye, and different cholesterol concentrations are pipetted onto the paper-sensor. Once the color is fully developed, a picture with a smartphone camera is taken. Tests are repeated to ensure consistent results and to find optimal dye/enzyme concentration. The smartphone image is analyzed using image software ImageJ. Image analysis indicate sensor accuracy and significant color differentiation between cholesterol concentrations.

Cholesterol is mixed in a detergent triton X-100, and then in 10 mM phosphate buffer solution (PBS) to yield cholesterol solutions of 50, 100, 150, 200, 250, 300, 400, 500 mg/dl. The dye tetramethylbenzidine (TMB) is mixed with DMSO (5.8 mg/ml).

A test sample of 15 μL of cholesterol solution is pipetted into a well of a 96-well plate, followed by 5 μL each of enzyme cholesterol oxidase (100 IU/ml), horseradish peroxidase (25 IU/ml), and dye TMB. The enzyme solutions are prepared in 10 mM PBS. The entire solution is then transferred to a chromatography paper strip (2 cm×0.7 cm).

Upon proving the chemistry of the sensor (100) to be reliable and accurate, the sensor is fabricated by an inkjet printer that is low-cost and scalable to mass production. A consumer grade modified inkjet printer costing less than $50 is retrofitted to print the desirable enzymatic mixture. The printer's covering assembly is removed to expose the cartridges, rails, and electronics beneath, and secure shut the paper clamp to trick the printer into printing the test strips. Surgical tubing is used to charge the ink, the cartridge's air pressure is increased to print smaller volumes and creates pseudo-cartridges to overcome the proprietary protections and modified ink cartridges to print the desired ink. Ten ink recipes were engineered to optimize flow dynamics and avoid recurrent problems with ink dripping and nozzle clogging while maximizing enzymatic sensitivity. To the desired ink, triton X-100 is added to eliminate bubbles that cause ink dripping and glycerol is added to increase the viscosity of ink to ensure an accurate print. Two printing systems have been tested: the piezoelectric Epson Workforce 30® and the thermal HP Deskjet 1010®. To ensure printing functionality, a blank ink (glycerol and $H_2O$) with fluorescent tracer Fluorescein is tested. The enzymatic ink is printed with one of three dyes: Tetramethylbenzidine (TMB), 4-Aminoantipyrine (4-AAP) or 10-Acetyl-3,7-dihydroxyphenoxazine (ADHP) to test which dye provided the greatest color differentiation. The inks are then printed onto Whatman Grade 1 qualitative analysis paper. The resultant test strips are tested with known concentrations of cholesterol, and once the color had fully developed, an image is taken on a smartphone or any image capturing device for later analysis.

Results:

FIGS. 4 through 6 show the metrics of color change against different cholesterol concentrations using three common color detection reagents, tetramethylbenzene (TMB), 4-aminoantipyrine (4-AAP), and 10-Acetyl-3,7-dihydroxyphenoxazine (ADHP), respectively. The 10-Acetyl-3,7-dihydroxyphenoxazine (ADHP) is commonly referred to as Amplex Red. As shown, all the three-color detection reagents are capable to detect the cholesterol concentrations in the range 100 to 400 milligrams per deciliter, the typical range in human blood. The color separation histograms in FIGS. 4 through 6 are obtained from photography using a smartphone. Histogram analysis was performed on the sensor's circular reaction zone ROI using ImageJ. A linear trend line is observed for cholesterol concentrations 100-400 mg/dL for all dyes, demonstrating a linear model for relating color intensity to cholesterol concentration ($R^2$>0.9). The image histogram analysis can hence provide a quantitative measure of the cholesterol concentrations present.

In FIG. 4, the green-blue color change is observed for TMB occurred rapidly, within 30 seconds of sample deposition. However, with higher concentrations (>300 mg/dL) double oxidation occurs, producing yellowed hues. Thus, it is suitable for mid-range concentrations since double oxidation occurs at concentrations >300 mg/dL producing spots with yellow hues.

In FIG. 5, the orange hued color change observed for 4-AAP, out of all three dyes, the slowest, taking about 6 minutes for full color development after sample deposition. However, it yields homogeneous color distribution, exhibits greater differentiation in the lower ranges of cholesterol, and does not double oxidize.

In FIG. 6, the magenta color change is observed for ADHP in 60 seconds which is slower than TMB, but quicker than 4-AAP. It is advantageous that the secondary color changing oxidations do not occur, unlike TMB. It also exhibits vibrant color differentiation well-suited for high concentrations.

The cost analysis shows a per-test cost of testing cholesterol using the proposed biosensor (100) is $0.02 which is about 200 times cheaper than current home tests and about 2000 times cheaper than current lab tests. One source of the cost-reduction over current tests is the novel usage of the inkjet printing technique, which reduces the waste of expensive enzyme and dye reagents as compared to traditional printing techniques.

Moreover, current lab tests take about 1 to 3 weeks of time to provide results whereas the proposed cholesterol biosensor (100) gives result much faster, with exact time-to-reading depending upon the selection of dye, ranging from 30 seconds to six minutes.

In conclusion, experimental results show the cholesterol biosensor (100) provides quantifiable color differentiation accurate for field use, across three dyes. The inkjet printer precisely places each droplet of ink, greatly conserving the use of expensive enzyme mixture whereas the traditional fabrication methods like dip coating and screen printing waste costly reagents.

OxLDL Colorimetric Test

Another embodiment of present invention is to provide an OxLDL colorimetric biosensor (200) for the colorimetric detection of OxLDL in a blood sample (600). The biosensor (200) is a portable, low-cost, paper-based sensing platform which detects OxLDL in blood using a colorimetric test. The biosensor (200) is fabricated by depositing iodide reagent ink (202) on detection test strip (201) using inkjet printer. The test strip (201) is a cellulosic substrate of Whatman Grade 1 qualitative filter paper which is capable of absorbing the reagents. It will be appreciated to those skilled in the art that, any other suitable substrate capable of absorbing the reagents may also be used.

FIG. 7A and FIG. 7B shows working of biosensor (200). The test strip and the iodide reagent ink (202) are placed in paper tray and ink cartridge of the inkjet printer respectively. The iodide reagent ink (202) is printed on the test strip (201) in a predetermined shape. The sample receiving region (203) is provided on the top area where the iodide reagent ink (202) is printed. When a blood sample (600) is placed over the sample receiving region (203), the biosensor (200) changes the color in the detection strip (201). The biosensor (200) utilizes an iodometric reaction shown below to detect lipid peroxides of OxLDL.

The resultant triiodide produces a yellow-brown color. The concentration of OxLDL in the sample is quantified using a calibration curve. The color fully develops in 30 minutes after which an image is taken on a smartphone or any imaging capturing device for RGB histogram analysis. The color change indicates the amount of OxLDL in blood sample (600). The biosensor (200) differentiates color for the high and low OxLDL concentrations.

Typically, the iodide reagent ink (202) comprises of: surfactant including triton X-100 and sodium n-dodecyl sulfate; humectant including glycerol and polyethylene glycol and iodide reagents including potassium phosphate and potassium iodide.

Hydrophobic reagent ink (500a) is optionally added to improve lateral flow characteristics, by limiting the region of flow on the test strip (201). The hydrophobic reagent ink (500a) is printed around the sample receiving region (203) on the substrate or solid surface using inkjet printer. The hydrophobic reagent ink (500a) comprises of: hydrophobic sizing agent including alkenyl succinic anhydride (ASA) to make certain regions of test strip (201) hydrophobic; organic solvent including acetone, benzene and hexanol to solubilize hydrophobic sizing agent; surfactant including triton X-100 and sodium n-dodecyl sulfate and humectant including glycerol and polyethylene glycol.

A red blood cell filter is optionally added on top of the sample receiving region (203) to remove the red blood cells, leaving only the blood plasma on the sample receiving region. The red blood cell filter is a lectin-treated and is of a narrow pore size. The red blood cell filter increases the accuracy of colorimetry to detect OxLDL by eliminating background colorations from red blood cells in the sample.

The substrate or solid surface (201) onto which reagents are applied by inkjet printing, may be a flat surface or may have depressions, such as, indentations, grooves and wells. The depressions are created by multilayer substrate where cutouts have been formed on some of the layers. The depositing of reagents into such depressions on the substrate or solid surface is accomplished by conveniently reprogramming the computer driving the inkjet printer. The inkjet printers produce droplets in the range of 2 to 4 Pico liters giving the ability to apply reagents uniformly and also to control the reagent film thickness precisely. This enables the development of accurate and repeatable detection test strips.

Experimental Data:

The biosensor (200) that is used to detect OxLDL accurately is prepared by taking a sheet of Whatman Grade 1 qualitative filter paper and pipetting iodide reagent ink (202) onto the cellulosic substrate. The iodide reagents potassium phosphate and potassium iodide are pipetted in quantity of 0.4M and 0.24M respectively. The biosensor (200) functions by detecting hydroperoxides. The biosensor (200) is first tested with hydrogen peroxide to confirm whether the sensor detects the lipid peroxides of OxLDL.

Once the color of the sensor fully develops, a picture is taken with a smartphone camera or any suitable image capturing device to ensure that the test can be performed at homes and health clinics. Varying concentrations of peroxide are tested to determine sufficient color differentiation. Tests are run several times to ensure reproducibility of results. After testing the sensor with hydrogen peroxide in range of 1 µM to 400 µM, the biosensor (200) is tested with actual OxLDL samples. Native LDL was oxidized and OxLDL samples were then tested at the 0, 1, and 2 hrs intervals.

Result:

After waiting for 30 min for color development, the test strips were photographed with a smartphone.

The colorimetric biosensor (200) is able to detect the hydrogen peroxide concentrations in the range of 50-400 mg/dL. The results for the iodometric sensor response to varying concentrations of hydrogen peroxides are seen in the FIG. 7C.

FIG. 7D shows the sensor response to progression of LDL's oxidation over time. It is seen that as oxidation progressed, the sensor responded with increasing color intensity. This change in color intensity was more apparent at the boundaries of the sensor. As with the hydrogen peroxide test samples, color differentiation is not great enough to warrant RGB image analysis. However, the sensor can alert users to high-low concentrations of OxLDL. Though less sensitive to OxLDL than the electrochemical sensor, the iodometric sensor is extremely inexpensive as the per-sensor cost is primarily the cost of the paper substrate due to the low cost of the reagents.

The cost analysis shows a per-test cost of testing OxLDL using the proposed colorimetric biosensor (200) is less than $0.01.

The biosensor (200) differentiates between low and high OxLDL concentrations. Furthermore, the biosensor (200) detects OxLDL in the earlier stages of its oxidation.

OxLDL Electrochemical Test:

Another embodiment of the present invention is to provide an electrochemical OxLDL biosensor (300) for quantitative measurement of OxLDL in a blood sample (600). The electrochemical detection of OxLDL requires an understanding of LDL oxidation. During early stages of oxidation, lipid peroxides are formed on the surface of the OxLDL prior to conformational changes in the apolipoprotein B. The lipid peroxides formed on the surface of the OxLDL molecule can then be detected through electronegative interactions with the working electrode (301) of the three-electrode system.

The working electrode (301) comprises of: functionalized carbon nanotubes (fCNTs) (302) having been functionalized via the addition of hydroxyl and carboxyl groups to the carbon nanotube structures. The carbon nanotubes (302) have high affinity towards lipids, allowing the nanotubes to move close to the target OxLDL molecule. The fCNTs (302) having hydroxyl and carboxyl groups which facilitate an electrochemical interaction between the fCNTs (302) and the lipid peroxide molecules on OxLDL.

FIG. 8, FIG. 9A and FIG. 9B represents working of electrochemical OxLDL biosensor (300) for detecting OxLDL. The measurement of OxLDL by electrochemical interaction is measured using sweeping voltammetry measurements. The sweeping voltammetry method uses a three-electrode system: a working electrode (301), a counter electrode (800), and a reference electrode (700). The fCNTs (302) are located on the working electrode (301). The blood sample (600) is placed on the blood sample receiving region (306) on the working electrode (301). The voltage between the reference and working electrode (301) is then varied over time and current is measured. The reference electrode (700) has a known reduction potential, which allows the voltage of the working electrode (301) to be measured accurately. No current flows between the reference and working electrode (301). The reference electrode (700) measures the voltage at the working electrode (301). The counter electrode (800) is used to measure the current to perform voltammetry. The counter electrode (800) is connected to the working electrode (301). Once the voltage reaches a reduction potential, electrons are released from the working electrode (301) and flow to the counter electrode (800). The output current is then correlated to the presence of lipid peroxide and OxLDL in the blood sample. The device that controls the variation of potential over time and measures the current is a potentiostat (303). The fCNT (302) working electrode is prepared by 1.) placing the fCNT (302) in an ink and then inkjet printing the fCNT onto a test strip substrate (302) or 2.) by coating a probe with fCNTs (302).

The counter electrode (800) can be made with a platinum (Pt) wire and the reference electrode (700) can be made with a Ag/AgCl wire.

When inkjet printing the fCNT sensors, a fCNT ink, counter electrode ink, and reference electrode ink must be fabricated. The fCNT ink comprises of: surfactant including triton X-100 and sodium n-dodecyl sulfate; humectant including glycerol and polyethylene glycol and fCNTs (302) with functional hydroxyl and carboxyl groups.

The counter electrode (800) ink further comprises of: surfactant including triton X-100 and sodium n-dodecyl sulfate; humectant including glycerol and polyethylene glycol and a counter electrode conducting compound or polymer including silver nanoparticles, graphene, or polyaniline. The conducting compound or polymer are capable of conducting electrons.

The reference electrode (700) ink further comprises of: surfactant including triton X-100 and sodium n-dodecyl sulfate; humectant including glycerol and polyethylene glycol and a reference electrode conducting compound or polymer including silver chloride. The conducting compound or polymer is capable of conducting electrons and form electrode with known electrode potential.

Hydrophobic reagent ink (500a) is optionally added to improve lateral flow characteristics by limiting the region of flow. The hydrophobic reagent ink (500a) is applied around the working electrode (401), the reference electrode (700) and the counter electrode (800). The hydrophobic reagent ink (500a) comprises of: hydrophobic sizing agent including alkenyl succinic anhydride (ASA) to make certain regions hydrophobic; organic solvent including acetone, benzene and hexanol to solubilize hydrophobic sizing agent; surfactant including triton X-100 and sodium n-dodecyl sulfate and humectant including glycerol and polyethylene glycol.

A red blood cell filter is optionally added on top of the fCNT (302) electrode to remove red blood cells, leaving only blood plasma on the detection area of the sensor. The red blood cell filter is a lectin-treated and has a narrow pore size. The red blood cell filter increases the accuracy of electrochemical biosensor to detect OxLDL by eliminating background electrochemical interactions with red blood cells that can interfere with the voltammetry process.

Experimental Data:

Three working electrodes have been investigated: fCNT, gold, and graphite (304). To establish the principle of detection, tests have been performed with hydrogen peroxide ($H_2O_2$) samples of varying concentrations. Only the fCNT electrode could detect peroxide at the micromolar concentrations of peroxides expected of OxLDL and was subsequently tested with actual OxLDL samples.

Phase 1: The electrochemical sensor requires 3-electrode system and electronics for measuring currents elicited by electrochemical charge transfers. For this purpose, an inexpensive potentiostat (303) was used to measure the small currents produced by the electrochemical reactions. The firmware of the potentiostat (303) was installed and a Java Runtime executable was activated for measurement.

The counter electrode (800) is made with a platinum (Pt) wire with the end coiled. A Ag/AgCl reference electrode was made by incubating silver wire in ferric chloride.

The CNTs are functionalized by immersion in an acid bath of nitric acid, sulfuric acid, and hydrogen peroxide for 5 hours. After filtration and several washes in distilled water, the fCNTs are dried at 300° C. temperature for 2 hours. To create the fCNT probe electrode, the tip of a transfer pipette with an embedded copper wire is evenly coated with an epoxy (305) and graphite (304) mixture and then coated in the fCNTs. Next, the exposed ends of the copper wire are tightly wrapped around the tip of the fCNT-coated probe.

Native LDL is purchased from Sigma Aldrich and oxidized in $CuSO_4$. 10 mL of a 5 µM solution of $CuSO_4$ is prepared to which 75 µL of native-LDL (40 mg/ml) solution was added. The resultant 0.3 mg/ml LDL/$CuSO_4$ solution is incubated in a water bath at 37° C. The sensor is tested by placing the 3 electrodes in an ELISA plate well containing 30 µl of OxLDL and initiating the glucose meter.

In addition to the fCNT (302) working electrode (301) of the Phase 1 tests, two other electrodes have also been tested. The ability of three electrode materials, gold, graphite (304) and fCNT, to detect various concentrations of hydrogen peroxide test solutions, have been performed. Potentiostat measurements for each test was obtained with cyclic voltammetry (CV) and linear sweep (LSV) voltammetry. Because only the functionalized carbon nanotube working electrode detected $H_2O_2$ at the desired concentrations, the fCNT electrode was then used in tests with native and oxidized LDL.

Results:

FIG. 10A and FIG. 10B respectively represents the sensitivity of the gold and graphite (304) standard electrodes compared to sensitivity of fCNT electrode as shown in FIG. 10C to peroxides. The fCNT electrode is able to detect peroxides at low concentrations of 0.22 µM, whereas graphite (304) and gold counterparts can only detect peroxides in the upper mM range. The fCNT detector's high sensitivity to ultra-low concentrations of peroxides demonstrate its potential for detecting lipid peroxides in OxLDL from blood samples, which are commonly found in low µM concentrations.

Having demonstrated its effectiveness, the fCNT electrode is then tested with actual OxLDL samples, instead of peroxides. As shown in FIG. 10D, fCNT sensor responds to native LDL at 0 hours and OxLDL oxidized for 1 hour and 2 hours. The sensor performs well, increasing current measurements as the oxidization of LDL progresses. The results confirm that the fCNT sensor can indeed detect OxLDL at concentrations found in blood samples and is responding to the formation of new lipid peroxides.

A cost analysis shows that the per test cost of the electrochemical OxLDL biosensor disclosed here is $20, at least 10 times cheaper than current lab-based ELISA test which costs more than $200.

Furthermore, the current lab-based ELISA tests take 3 to 4 weeks of time to provide results whereas the proposed electrochemical biosensor gives result in 35 seconds.

Cholesterol Electrochemical Test:

Another embodiment of the present invention is to provide an electrochemical cholesterol biosensor (400) for quantitative measurement of cholesterol in a blood sample (600).

FIG. 11A and FIG. 11B shows working of electrochemical cholesterol biosensor (400) for detecting cholesterol. The measurement of cholesterol by electrochemical interaction is measured by using sweeping voltammetry measurements. The sweeping voltammetry method uses a three-electrode system: a working electrode (401), a counter electrode (800), and a reference electrode (700). In the electrochemical cholesterol test, hydrogen peroxide is produced by cholesterol oxidase in the enzyme mixture (402). The working electrode (401) comprises of the enzyme mixture (402) and the conducting ink (403) deposited onto the testing substrate. The blood sample (600) is placed on sample receiving region (405) which is the working electrode (401). The voltage between the reference and working electrode (401) is varied over time and current is measured. The reference electrode (700) has a known reduction potential, which allows the voltage of the working electrode (401) to be accurately measured. No current flows between the reference electrode (700) and working electrode (401). The reference electrode (700) purely measures the voltage at the working electrode (401). The counter electrode (800) is used to measure the current to perform voltammetry. The counter electrode (800) is typically connected to the working electrode (401). This hydrogen peroxide is then measured by reduction-oxidation reaction (redox reaction). The redox reaction happens at a reduction potential which is reached by altering the voltage through voltammetry. After the redox reaction, electrons are released, thereby creating a current which can be measured. The device that controls the variation of potential over time and measures the current is a potentiostat.

The enzyme mixture (402) comprises of: Ionic salt buffer solution; surfactant including triton X-100 and sodium n-dodecyl sulfate; humectant including glycerol and polyethylene glycol and enzymes including horseradish peroxide, cholesterol oxidase, glucose oxidase and cholesterol esterase to detect cholesterol. The ionic salt buffer solution includes phosphate buffer saline to preserve protein structures.

The counter electrode (800) ink further comprises of: surfactant including triton X-100 and sodium n-dodecyl sulfate; humectant including glycerol and polyethylene glycol and counter electrode (800) conducting compound or polymer including silver nanoparticles, graphene, or polyaniline. The conducting compound or polymer are capable of conducting electrons.

The reference electrode (700) ink further comprises of: surfactant including triton X-100 and sodium n-dodecyl sulfate; humectant including glycerol and polyethylene glycol and reference electrode (700) conducting compound or polymer including silver chloride. The conducting compound or polymer is capable of conducting electrons and that forms an electrode with known electrode potential.

Hydrophobic reagent ink (500a) is optionally added to improve the lateral flow characteristics by limiting the region of flow. The hydrophobic reagent ink (500a) is applied around the working, reference and counter electrode (800). The hydrophobic reagent ink (500a) comprises of: hydrophobic sizing agent including alkenyl succinic anhydride (ASA) to make certain regions hydrophobic; organic solvent including acetone, benzene and hexanol to solubilize hydrophobic sizing agent; surfactant including triton X-100 and sodium n-dodecyl sulfate and humectant including glycerol and polyethylene glycol.

A red blood cell filter is optionally added on top of the working electrode (401) to remove red blood cells, leaving only blood plasma on the sample region. The red blood cell filter is a lectin-treated and has a narrow pore size. The red blood cell filter increases the accuracy of electrochemical biosensor (400) to detect cholesterol by eliminating background electrochemical interactions with red blood cells that can interfere with the voltammetry process.

The cost analysis shows a per test cost of testing cholesterol using the electrochemical biosensor (400) of $0.05-$0.10. Furthermore, the proposed electrochemical biosensor (400) provides results within 30 seconds.

In the above-mentioned biosensors, the reagent ink is of a rheology of high shear thinning liquid dynamics and a specific viscosity to enable high-velocity jet inkjet processing resulting in high strain rate deformation with dominant extensional behavior;

In the above-mentioned biosensors, the surfactant is contained with the reagent ink to alter the dynamic surface tension of the reagent ink such that interfacial tension during inkjet printing allows droplet formation;

In the above-mentioned biosensors, the thickening humectant, including glycerol and polyethylene glycol, is contained within the reagent ink to ensure the mixture is of a viscosity such that viscoelastic stresses resist the backward motion of liquid filament formation during which surface tension forms the spherical shape of the reagent ink droplet, emerging from the inkjet printer's nozzles.

In the above-mentioned biosensors, the thickening humectant forms a strengthened hydrogen-bond network in the reagent ink, minimizing evaporation of the reagent ink;

The proposed biosensors developed in the present invention enables a holistic assessment of cardiac disease risk. The said biosensors closely monitor atherosclerotic progression by measuring cholesterol and OxLDL levels in patient.

Any alterations and further modifications in the described invention by one skilled in the art, and any further applications of the principles of the present invention as described herein are considered a part of this present invention.

Cholesterol Colorimetric Test
100—Cholesterol colorimetric biosensor
101—Detection strip
102—Enzyme mixture reagent
103—Color detection reagent
104—Sample receiving region
105—Enzyme mixture and color detector reagent printed as a circle on the substrate or solid support
106—Enzyme mixture and color detector reagent change in color when a sample of blood is introduced OxLDL Colorimetric Test
200—OxLDL colorimetric biosensor
201—Detection test strip/substrate or solid support
202—Iodide reagent ink
203—Sample receiving region OxLDL Electrochemical Test:
300—OxLDL electrochemical biosensor
301—Working electrode
302—Functionalized carbon nanotubes (fCNTs)
303—Potentiostat
304—Graphite
305—Epoxy
306—Sample Receiving Region Cholesterol Electrochemical Test:
400—Cholesterol electrochemical biosensor
401—working electrode 402—Enzyme mixture
403—Conducting ink
404—Potentiostat
405—Sample receiving region
500—Hydrophobic region
500a—Hydrophobic ink
600—Blood sample
700—Reference Electrode
800—Counter Electrode

The invention claimed is:

1. A process for the preparation of a colorimetric cholesterol biosensor (100), electrochemical cholesterol biosensor (400), colorimetric OxLDL biosensor (200), and electrochemical OxLDL biosensor (300), the process comprising of:
placing a diagnostic test strip (101) in an inkjet printer paper tray wherein the diagnostic test strip is a flat surface or with depressions selected from indentations, grooves and wells;
placing a hydrophobic reagent ink in an ink cartridge of the inkjet printer and printing the hydrophobic reagent ink around a sample receiving region on the diagnostic test strip using the inkjet printer;
optionally adding a red blood cell filter on top of the sample receiving region;
and placing a blood sample over the sample receiving region and allowing for colorimetric or electrochemical reaction to take place on the diagnostic test strip to enable quantitative detection of OxLDL or cholesterol.

2. The process of claim 1, wherein the biosensor prepared is a colorimetric cholesterol biosensor (100) that quantifies the cholesterol concentration within a blood sample via colorimetric means, the process further comprising:
placing an enzyme mixture reagent (102) in the ink cartridge of the inkjet printer and printing the enzyme mixture reagent (102) on the diagnostic test strip (101) in a predetermined shape using the inkjet printer;
placing a color detection reagent (103) in the ink cartridge of the inkjet printer and printing the color detection reagent (103) over the enzyme mixture reagent (102) on diagnostic test strip (101) using the inkjet printer;
placing a blood sample (600) over the sample receiving region (104) and allowing the color change of the sample receiving region (104) depending upon the concentration of cholesterol; and
taking an image of the resulted diagnostic test strip (101) on a smartphone or other imaging platform for RGB histogram analysis and quantifying the concentration of cholesterol in the blood sample (600).

3. The process of claim 2, wherein the enzyme mixture reagent (102) and the color detection reagent (103) can also be printed on the diagnostic test strip (101) as a single mixture in the form of a reagent ink.

4. The process of claim 1, wherein the biosensor prepared is a colorimetric OxLDL biosensor (200) that quantifies the OxLDL concentration within a blood sample via colorimetric means, the process further comprising:
placing an iodide reagent ink (202) in the ink cartridge of the inkjet printer and printing the iodide reagent ink (202) on the diagnostic test strip (101) in a predetermined shape using the inkjet printer,
optionally adding a red blood cell filter on top of the sample receiving region (203);
placing a blood sample (600) over the sample receiving region (203) and allowing the color change of the sample receiving region (203) depending upon the concentration of OxLDL; and
taking an image of the resulted diagnostic test strip (101) on a smartphone or other imaging platform for RGB histogram analysis and quantifying the concentration of OxLDL in the blood sample (600).

5. The process of claim 1, wherein the inkjet printer prints ink droplets in the range of 2 to 4 picoliters and employs thermal or piezoelectric droplet dispersion mechanisms.

6. The process of claim 1, wherein the biosensor prepared is an electrochemical OxLDL biosensor (300) that quantifies the OxLDL concentration within a blood sample via electrochemical means, the process further comprising:
preparing a working electrode by putting functionalized carbon nanotube (fCNT) (302) in an fCNTs ink and then inkjet printing the fCNT (302) or by placing the fCNT (302) electrode on a probe;
placing a blood sample (600) over a sample receiving region (306);
facilitating an electrochemical interaction between the fCNT (302) and lipid peroxide molecules on OxLDL;
measuring the electrochemical interaction between the fCNT (302) and the lipid peroxide molecules on OxLDL using sweeping voltammetry method;
varying the voltage between a reference electrode (700) and working electrode (301) and measuring the current with a potentiostat (303);
releasing electrons from the working electrode (301) to the counter electrode (800) as the voltage reaches a reduction potential and
correlating the output current to the presence of lipid peroxide and OxLDL in the blood sample.

7. The process of claim 1, wherein the biosensor prepared is an electrochemical cholesterol biosensor (400) that quantifies the cholesterol concentration within a blood sample via electrochemical means, the process further comprising:
preparing a working electrode by putting an enzyme mixture (402) in conducting ink (403);
placing a blood sample (600) over a sample receiving region (405);
facilitating an electrochemical interaction between the enzyme mixture (402) and cholesterol;
measuring the electrochemical interaction between the enzyme mixture (402) and cholesterol using sweeping voltammetry method;
varying the voltage between a reference electrode (700) and working electrode (401) and measuring the current with potentiostat (303);
releasing electrons from the working electrode (401) to the counter electrode (800) as the voltage reaches a reduction potential and
correlating the output current to the presence of cholesterol in the blood sample (600).

* * * * *